United States Patent
El A'mma et al.

(10) Patent No.: US 8,197,836 B2
(45) Date of Patent: Jun. 12, 2012

(54) SOLID MICROBICIDAL COMPOSITION

(75) Inventors: Beverly Jean El A'mma, Perkiomenville, PA (US); Randall Wayne Stephens, Perkasie, PA (US)

(73) Assignee: Rohm and Haas Company, Philadelphia, PA (US)

( * ) Notice: Subject to any disclaimer, the term of this patent is extended or adjusted under 35 U.S.C. 154(b) by 66 days.

(21) Appl. No.: 12/826,729

(22) Filed: Jun. 30, 2010

(65) Prior Publication Data

US 2011/0003871 A1 Jan. 6, 2011

Related U.S. Application Data

(60) Provisional application No. 61/269,980, filed on Jul. 1, 2009.

(51) Int. Cl.
*A01N 25/08* (2006.01)
(52) U.S. Cl. ..... 424/409; 424/408; 424/400; 514/222.2; 514/183
(58) Field of Classification Search ........................ None
See application file for complete search history.

(56) References Cited

U.S. PATENT DOCUMENTS

| 3,870,795 | A | 3/1975 | Miller et al. |
| 5,185,356 | A | 2/1993 | Backhouse et al. |
| 6,241,994 | B1 * | 6/2001 | Lee et al. ................ 424/408 |
| 2007/0281043 | A1 | 12/2007 | Bergbauer et al. |

FOREIGN PATENT DOCUMENTS

JP 63215601 9/1988

OTHER PUBLICATIONS

Rohm and Haas, "Kathon (TM) CG", p. 4, fig. 2 (2006).
Archibald, "The System Magnesium Sulfate-Sodium Sulfate-Water and a Method for the Separation of the Salts", J. AM. Chem. Soc, vol. 46, No. 8, pp. 1760-1771 (1924).

* cited by examiner

*Primary Examiner* — Brandon Fetterolf
*Assistant Examiner* — Theodore R West
(74) *Attorney, Agent, or Firm* — Kenneth Crimaldi

(57) ABSTRACT

A solid microbicidal composition containing a mixture of 5-chloro-2-methyl-4-isothiazolin-3-one and 2-methyl-4-isothiazolin-3-one, magnesium sulfate, a metal nitrate, magnesium chloride, and water.

9 Claims, No Drawings

SOLID MICROBICIDAL COMPOSITION

This application claims the benefit of priority under 35 U.S.C. §119(e) of U.S. Provisional Patent Application No. 61/269,980 filed on Jul. 1, 2009.

This invention relates to stable solid microbicidal compositions containing 5-chloro-2-methylisothiazolin-3-one and 2-methylisothiazolin-3-one.

A solid composition containing a preservative and a water soluble inorganic salt is disclosed in JP S63-215601. The composition may contain a variety of preservatives, including 5-chloro-2-methylisothiazolin-3-one and 2-methylisothiazolin-3-one, and a variety of water soluble inorganic salts. However, this reference does not disclose water soluble inorganic salts capable of providing a stable solid composition containing 5-chloro-2-methylisothiazolin-3-one and 2-methylisothiazolin-3-one.

The problem addressed by this invention is to provide a stable solid composition containing 5-chloro-2-methylisothiazolin-3-one and 2-methylisothiazolin-3-one.

STATEMENT OF THE INVENTION

The present invention is directed to a solid microbicidal composition comprising: (a) 2.5-9.5 wt % of a mixture of 5-chloro-2-methyl-4-isothiazolin-3-one and 2-methyl-4-isothiazolin-3-one; (b) 67-90 wt % magnesium sulfate, on an anhydrous basis; (c) 1.4-5.5 wt % of a metal nitrate, on an anhydrous basis; (d) 0.9-3.5 wt % magnesium chloride, on an anhydrous basis; and (e) 4-16 wt % water.

The present invention is further directed to a solid microbicidal composition comprising: (a) 2.5-5.5 wt % of a mixture of 5-chloro-2-methyl-4-isothiazolin-3-one and 2-methyl-4-isothiazolin-3-one; (b) 60-85 wt % magnesium sulfate, on an anhydrous basis; (c) 3.7-8 wt % of a metal nitrate, on an anhydrous basis; (d) 1.2-2.5 wt % magnesium chloride, on an anhydrous basis; and (e) 10-22 wt % water.

The present invention is directed to a solid microbicidal composition comprising: (a) 2.5-26 wt % of 2-methyl-4-isothiazolin-3-one; (b) 48-95 wt % magnesium sulfate, on an anhydrous basis; and (e) 2.5-26 wt % water.

The present invention is further directed to a method for producing a solid microbicidal composition comprising: (a) 2.5-9.5 wt % of a mixture of 5-chloro-2-methyl-4-isothiazolin-3-one and 2-methyl-4-isothiazolin-3-one; (b) 67-90 wt % magnesium sulfate, on an anhydrous basis; (c) 1.4-5.5 wt % of a metal nitrate, on an anhydrous basis; (d) 0.9-3.5 wt % magnesium chloride, on an anhydrous basis; and (e) 4-16 wt % water. The method comprises combining 67-90 wt % magnesium sulfate and 10-33 wt % of an aqueous biocide composition comprising (i) 25-35 wt % of a mixture of 5-chloro-2-methyl-4-isothiazolin-3-one and 2-methyl-4-isothiazolin-3-one; (ii) 10-22 wt % of a metal nitrate; (iii) 8-14 wt % magnesium chloride; and (iv) 35-50 wt % water.

DETAILED DESCRIPTION OF THE INVENTION

"MI" is 2-methyl-4-isothiazolin-3-one, also referred to by the name 2-methyl-3-isothiazolone. "CMI" is 5-chloro-2-methyl-4-isothiazolin-3-one, also referred to by the name 5-chloro-2-methyl-3-isothiazolone. Preferably, the weight ratio of CMI to MI is at least 1:1, alternatively at least 2:1. Preferably, the weight ratio of CMI to MI is no greater than 4:1. In one preferred embodiment of the invention, the CMI: MI ratio is about 3:1.

As used herein, the following terms have the designated definitions, unless the context clearly indicates otherwise.

The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. A "solid" composition as the term is used herein is one that is solid at 25° C. The following abbreviations are used throughout the specification: ppm=parts per million by weight (weight/weight), mL=milliliter, AI=active ingredient, i.e., total amount of isothiazolones. Unless otherwise specified, temperatures are in degrees centigrade (° C.), and references to percentages are percentages by weight (wt %). Percentages of water in the solid compositions include all water present in any hydrated salts and any free water that may be present.

A "metal nitrate" preferably is a nitrate salt of an alkali metal, an alkaline earth metal, or ammonium. Preferably, the metal is lithium, sodium, potassium, magnesium, calcium, ammonium, or a combination thereof; more preferably sodium, potassium, magnesium, or combinations thereof. Magnesium is especially preferred.

In some embodiments of the invention in which the solid composition contains from 2.5-9.5 wt % of a mixture of CMI and MI, the solid composition contains at least 4 wt % of said mixture, alternatively at least 5 wt %, alternatively at least 6 wt %; the solid composition contains no more than 9 wt % of said mixture, alternatively no more than 8.5 wt %, alternatively no more than 8 wt %. In some embodiments of the invention in which the solid composition contains from 67-90 wt % magnesium sulfate, on an anhydrous basis, the solid composition contains at least 68 wt %, alternatively at least 69 wt %, alternatively at least 70 wt %, alternatively at least 71 wt %, alternatively at least 72 wt %; the solid composition contains no more than 85 wt % magnesium sulfate, alternatively no more than 80 wt %. In some embodiments of the invention in which the solid composition contains from 1.4-5.5 wt % of a metal nitrate, the solid composition contains at least 2.3 wt % metal nitrate, alternatively at least 3 wt %, alternatively at least 3.4 wt %; the solid composition contains no more than 5 wt % metal nitrate, alternatively no more than 4.8 wt %, alternatively no more than 4.6 wt %. In some embodiments of the invention in which the solid composition contains from 0.9-3.5 wt % magnesium chloride, the solid composition contains at least 1.3 wt % magnesium chloride, alternatively at least 1.8 wt %, alternatively at least 2.1 wt %; the solid composition contains no more than 3.2 wt % magnesium chloride, alternatively no more than 3 wt %, alternatively no more than 2.9 wt %. In some embodiments of the invention in which the solid composition contains from 4-16 wt % water, the solid composition contains at least 6.5 wt % water, alternatively at least 8 wt %, alternatively at least 10 wt %; the solid composition contains no more than 15 wt % water, alternatively no more than 14 wt %, alternatively no more than 13 wt %.

In some embodiments of the invention in which the solid composition contains from 2.5-5.5 wt % of a mixture of CMI and MI, the solid composition contains at least 3 wt % of said mixture, alternatively at least 3.5 wt %, alternatively at least 4 wt %; the solid composition contains no more than 5.2 wt % of said mixture, alternatively no more than 5 wt %. In some embodiments of the invention in which the solid composition contains from 60-85 wt % magnesium sulfate, the solid composition contains at least 63 wt % magnesium sulfate, alternatively at least 64 wt %; the solid composition contains no more than 80 wt % magnesium sulfate, alternatively no more than 75 wt %. In some embodiments of the invention in which the solid composition contains from 3.7-8 wt % of a metal nitrate, the solid composition contains at least 4.3 wt % metal nitrate, alternatively at least 5 wt %, alternatively at least 5.7 wt %; the solid composition contains no more than 7.4 wt %, alternatively no more than 7.1 wt %. In some embodiments of the invention in which the solid composition contains from 1.2-2.5 wt % magnesium chloride, the solid composition contains at least 1.3 wt % magnesium chloride, alternatively at least 1.5 wt %, alternatively at least 1.7 wt %; the solid composition contains no more than 2.2 wt % magnesium chloride, alternatively no more than 2.1 wt %. In some embodiments of the invention in which the solid composition contains from 10-22 wt % water, the solid composition contains at least 13 wt % water, alternatively at least 15 wt %, alternatively at least 17 wt %; the solid composition contains no more than 15 wt % water, alternatively no more than 22 wt %, alternatively no more than 21.5 wt %.

In some embodiments of the invention in which the solid composition contains from 2.5-26 wt % of a mixture of CMI and MI, the solid composition contains at least 5 wt % of said mixture, alternatively at least 10 wt %; the solid composition contains no more than 24 wt % of said mixture, alternatively no more than 20 wt %. In some embodiments of the invention in which the solid composition contains from 48-95 wt % magnesium sulfate, the solid composition contains at least 51 wt % magnesium sulfate, alternatively at least 60 wt %; the solid composition contains no more than 90 wt % magnesium sulfate, alternatively no more than 80 wt %. In some embodiments of the invention in which the solid composition contains from 2.5-26 wt % water, the solid composition contains at least 5 wt % water, alternatively at least 10 wt %; the solid composition contains no more than 24 wt % of water, alternatively no more than 20 wt %.

The solid composition may contain traces of organic solvents carried over from production of the isothiazolone biocides. Preferably the total level of organic solvents in the solid composition is no more than 3%, alternatively no more than 2%, alternatively no more than 1%, alternatively no more than 0.7%, alternatively no more than 0.5%. Typical organic solvents which may be present include, e.g., ethanol, ethyl acetate, acetic acid, butyl acetate, butanol and methylene chloride.

In the method of this invention, the magnesium sulfate and the aqueous biocide composition are blended thoroughly to ensure that the magnesium sulfate is hydrated to the maximum extent possible. Examples of equipment that can be used for mixing include any equipment suitable for blending liquids and solids, e.g., screw mixers and ribbon blenders. Preferably, the mixture is not dried significantly during or after blending, i.e., no more than 5% of the water in the mixture is removed, alternatively no more than 2%, alternatively no more than 1%, alternatively no more than 0.5%, alternatively no more than 0.3%.

In some embodiments of the invention, the aqueous biocide composition used in the method contains at least 26% of a mixture of CMI and MI, alternatively at least 27%, alternatively at least 27.5%, alternatively at least 28%; the composition contains no more than 33% CMI/MI, alternatively no more than 32%, alternatively no more than 31%, alternatively no more than 30%, alternatively no more than 29%. In some embodiments of the invention, the amount of metal nitrate in the aqueous biocide composition is at least 11%, alternatively at least 12%, alternatively at least 15%; the amount of metal nitrate is no more than 27%, alternatively no more than 25%, alternatively no more than 22%, alternatively no more than 20%, alternatively no more than 18%. In some embodiments of the invention, the amount of magnesium chloride in the aqueous composition is at least 8.5%, alternatively at least 9%; the amount of magnesium chloride is no more than 13.5%, alternatively no more than 13%, alternatively no more than 12.5%, alternatively no more than 12%. In some embodiments of the invention, the aqueous biocide composition comprises no more than 48% water, alternatively no more than 47%; the amount of water is at least 38%, alternatively at least 40%. In some embodiments, this aqueous biocide composition contains organic solvents at a level no greater than 5%, alternatively no more than 4%, alternatively no more than 3%, alternatively no more than 2.5%, alternatively no more than 2%. Typical organic solvents which may be present include, e.g., ethanol, ethyl acetate, acetic acid, butyl acetate, butanol and methylene chloride.

In some embodiments of the invention, the aqueous biocide composition contains 10-20 wt % of a mixture of CMI and MI, 14-29 wt % metal nitrate, 3.5-9 wt % magnesium chloride and 40-80 wt % water. In some embodiments, the aqueous biocide composition contains at least 11% of a mixture of CMI and MI, alternatively at least 12%, alternatively at least 13%; the composition contains no more than 18% CMI/MI, alternatively no more than 17%, alternatively no more than 16%. In some embodiments of the invention, the amount of metal nitrate in the aqueous biocide composition is at least 15%, alternatively at least 16%, alternatively at least 17%, alternatively at least 18%; the amount of metal nitrate is no more than 27%, alternatively no more than 25%, alternatively no more than 23%, alternatively no more than 22%. In some embodiments of the invention, the aqueous biocide composition contains at least 4% magnesium chloride, alternatively at least 4.5%, alternatively at least 5%; the composition contains no more than 8% magnesium chloride, alternatively no more than 7.5%, alternatively no more than 7%. In some embodiments of the invention, the aqueous biocide composition comprises no more than 75% water, alternatively no more than 70%, alternatively no more than 65%; the amount of water is at least 45%, alternatively at least 50%. In some embodiments, this aqueous biocide composition contains organic solvents at a level no greater than 5%, alternatively no more than 4%, alternatively no more than 3%, alternatively no more than 2.5%, alternatively no more than 2%. Typical organic solvents which may be present include, e.g., ethanol, ethyl acetate, acetic acid, butyl acetate, butanol and methylene chloride. The present invention is also directed to a method for producing a solid composition comprising: (a) 2.5-5.5 wt % of a mixture of 5-chloro-2-methyl-4-isothiazolin-3-one and 2-methyl-4-isothiazolin-3-one; (b) 60-85 wt % magnesium sulfate, on an anhydrous basis; (c) 3.7-8 wt % of a metal nitrate, on an anhydrous basis; (d) 1.2-2.5 wt % magnesium chloride, on an anhydrous basis; and (e) 10-22 wt % water. The method comprises combining 60-85 wt % magnesium sulfate, on an anhydrous basis, with 15-40 wt % of the aqueous biocide composition containing 10-20 wt % of a mixture of CMI and MI.

In some embodiments of the invention, the aqueous biocide composition contains 40-60 wt % of MI and 40-60 wt % water. In some embodiments the aqueous biocide composition contains at least 45% MI, alternatively at least 48%; the composition contains no more than 55% MI, alternatively no more than 52%. In some embodiments the aqueous biocide composition contains at least 45% water, alternatively at least 48%; the composition contains no more than 55% water, alternatively no more than 52%. In some embodiments, this aqueous biocide composition contains organic solvents at a level no greater than 5%, alternatively no more than 4%, alternatively no more than 3%, alternatively no more than 2.5%, alternatively no more than 2%. Typical organic solvents which may be present include, e.g., ethanol, ethyl acetate, acetic acid, butyl acetate, butanol and methylene chloride. The present invention is also directed to a method for producing a solid composition comprising 2.5-26 wt % of MI; 48-95 wt % magnesium sulfate, on an anhydrous basis; and 2.5-26 wt % water. The method comprises combining 48-95 wt % magnesium sulfate, on an anhydrous basis, with 5-52 wt % of the aqueous biocide composition containing 40-60 wt % MI.

Magnesium sulfate may be used in its anhydrous form or in the form of a partial hydrate. The amounts specified are on an anhydrous basis, so if a partial hydrate is used, the amount of partial hydrate will be larger than the amount of anhydrous magnesium sulfate. Preferably, the magnesium sulfate is substantially anhydrous.

In one embodiment, the aqueous composition further comprises a copper salt as a stabilizer. Preferred copper salts are copper nitrate and copper sulfate, in amounts from 1 to 200 ppm of copper.

In one embodiment of the invention, the composition is substantially free of bromic acid, iodic acid, periodic acid or their salts, i.e., the composition contains less than 0.01% of these substances, alternatively less than 0.005%, alternatively less than 0.001%.

The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

EXAMPLES

The aqueous biocide compositions used in the present examples are as follows:

|   | AI | $Mg(NO_3)_2$ | $MgCl_2$ | water |
|---|---|---|---|---|
| Aq. biocide A | 28% CMI/MI | 16% | 9.5% | 46.5% |
| Aq. biocide B | 14% CMI/MI | 20% | 6% | 60% |
| Aq. biocide C | 50% MI | — | — | 50% |

Each biocide contained a 3:1 weight ratio of CMI/MI, except biocide C, which contained only MI. "AI" is the total amount of CMI and MI, as applicable. All work described herein was performed at room temperature (20-25° C.). Water was not removed from the compositions produced other than trace amounts lost to evaporation.

Example 1

Aqueous biocide A was combined with anhydrous magnesium sulfate in the proportions indicated below and the solid was compressed into tablets with the stated results.

| wt ratio A:$MgSO_4$ | tablet quality | % CMI/MI | % $H_2O$ | % $Mg(NO_3)_2$ |
|---|---|---|---|---|
| 35:65 | slightly moist | 9.80 | 16.3 | 5.60 |
| 30:70 | dry | 8.40 | 14.0 | 4.80 |
| 25:75 | dry | 7.00 | 11.6 | 4.00 |

The procedure for blending biocide A and magnesium sulfate is illustrated by the following sample run. 15.0 lbs (6.8 kg) of anhydrous magnesium sulfate having an average mesh size of 70 microns (Kali Chemical Co.) were charged to a BEPEX ribbon blender. The ribbon blender was equipped with a PVC drip tube which spanned the width of the blender in order to gradually drip in the liquid Biocide A during the mixing process. The blender speed was set at 70. Once the blender was running, one quarter (1.25 lbs, 0.57 kg) of the total Biocide A (5.0 lbs, 2.3 kg) was added slowly into the blender, letting the blender run for 5 minutes. The same blending sequence was repeated with the second quarter of the Biocide A in the blender and run for 5 minutes. The same blending was repeated with Biocide A addition at each quarter until all of the Biocide A was in the blender. When the final addition had been completed, the blender was run for 10 minutes. At the end of the blend, the dry, flowable material was transferred to pails and the transferred to a BALDWIN 20 Tablet Press for tabletting.

Comparative Example 1

Aqueous biocide A was combined with anhydrous sodium sulfate in the proportions indicated below and mixed thoroughly. The solid was evaluated as shown immediately and after 24 hours at room temperature (ca. 20-25° C.).

| wt ratio A:$Na_2SO_4$ | appearance immediate | after 24 hrs. | % CMI/MI |
|---|---|---|---|
| 25:75 | very wet | very wet | 7 |
| 21.4:78.3 | very wet | very wet | 6 |
| 17.8:82.2 | very wet | very wet | 5 |
| 14.38:85.62 | wet | wet | 4 |
| 10.71:89.29 | wet | wet | 3 |
| 7.14:92.86 | wet | slightly wet | 2 |
| 3.57:96.43 | slightly wet | very slightly wet* | 1 |

*possibly could form a tablet

Example 2

Aqueous biocides B and C were combined with anhydrous magnesium sulfate with mixing until a dry flowable solid was obtained.

| biocide | wt., g | MgSO$_4$, g | % MgSO$_4$ | AI | % water | % Mg(NO$_3$)$_2$ |
|---|---|---|---|---|---|---|
| B | 5.0 | 7.91 | 61% | 5.46% CMI/MI | 23.2% | 7.75% |
| C | 5.0 | 4.75 | 49% | 25.5% MI | 25.5% | 0 |

Comparative Example 2

Biocides B and C combined with anyhydrous sodium sulfate in the same amounts, as shown below. In each case a wet solid which would not flow was obtained.

| biocide | wt., g | Na$_2$SO$_4$, g | % Na$_2$SO$_4$ | AI |
|---|---|---|---|---|
| B | 5.0 | 7.91 | 61% | 5.46% CMI/MI |
| C | 5.0 | 4.75 | 49% | 25.5% MI |

The results described above would not have been expected because sodium sulfate absorbs more water per unit weight than magnesium sulfate. One kilogram of sodium sulfate (7.04 moles) absorbs 70.4 moles of water to form sodium sulfate decahydrate, or 1.27 kg water/kg sodium sulfate. One kilogram of magnesium sulfate (8.31 moles) absorbs 58.15 moles of water to form magnesium sulfate heptahydrate, or only 1.05 kg water/kg magnesium sulfate. Therefore, there would have been no reason to expect aqueous biocide compositions to form solids with much smaller amounts of magnesium sulfate, relative to sodium sulfate.

Example 3

Stability of Solid Compositions Containing MgSO$_4$ and Na$_2$SO$_4$

|  | Weeks Stored | Temp, °C. | % CMI/MI | % CMI/MI Remaining |
|---|---|---|---|---|
| 50% Biocide A, 50% Na$_2$SO$_4$ | 0 | 25 | 1.50 | 100% |
|  | 2 | 40 | 1.38 | 93% |
|  | 4 | 40 | 1.29 | 88% |
|  | 12 | 40 | 0.75 | 54% |
|  | 2 | 55 | 1.25 | 86% |
|  | 4 | 55 | 0.84 | 62% |
|  | 12 | 55 | 0.00 | 0% |
| 50% Biocide A, 50% MgSO$_4$ | 0 | 25 | 1.32 | 100% |
|  | 2 | 40 | 1.31 | 100% |
|  | 4 | 40 | 1.30 | 99% |
|  | 12 | 40 | 1.28 | 98% |
|  | 2 | 55 | 1.26 | 96% |
|  | 4 | 55 | 1.30 | 100% |
|  | 12 | 55 | 1.18 | 93% |

The invention claimed is:

1. A solid microbicidal composition comprising:
   (a) 2.5-9.5 wt % of a mixture of 5-chloro-2-methyl-4-isothiazolin-3-one and 2-methyl-4-isothiazolin-3-one;
   (b) 67-90 wt % magnesium sulfate, on an anhydrous basis;
   (c) 1.4-5.5 wt % of a metal nitrate, on an anhydrous basis;
   (d) 0.9-3.5 wt % magnesium chloride, on an anhydrous basis; and
   (e) 4-16 wt % water.

2. The composition of claim 1 having 4-8.5 wt % of a mixture of 5-chloro-2-methyl-4-isothiazolin-3-one and 2-methyl-4-isothiazolin-3-one; 69-85 wt % magnesium sulfate, on an anhydrous basis; (c) 2.3-4.8 wt % of a metal nitrate, on an anhydrous basis; (d) 1.3-3 wt % magnesium chloride, on an anhydrous basis; and (e) 6.5-14 wt % water.

3. The composition of claim 2 in which the metal nitrate is magnesium nitrate.

4. The composition of claim 3 in which 5-chloro-2-methyl-4-isothiazolin-3-one and 2-methyl-4-isothiazolin-3-one are in a weight ratio from 2:1 to 4:1.

5. A method for producing a solid microbicidal composition comprising: (a) 2.5-9.5 wt % of a mixture of 5-chloro-2-methyl-4-isothiazolin-3-one and 2-methyl-4-isothiazolin-3-one; (b) 67-90 wt % magnesium sulfate, on an anhydrous basis; (c) 1.4-5.5 wt % of a metal nitrate, on an anhydrous basis; (d) 0.9-3.5 wt % magnesium chloride, on an anhydrous basis; and (e) 4-16 wt % water; said method comprising combining 67-90 wt % magnesium sulfate and 10-33 wt % of an aqueous biocide composition comprising (i) 25-35 wt % of a mixture of 5-chloro-2-methyl-4-isothiazolin-3-one and 2-methyl-4-isothiazolin-3-one; (ii) 10-22 wt % of a metal nitrate; (iii) 8-14 wt % magnesium chloride; and (iv) 35-50 wt % water.

6. The method of claim 5 in which the solid microbicidal composition comprises: 4-8.5 wt % of a mixture of 5-chloro-2-methyl-4-isothiazolin-3-one and 2-methyl-4-isothiazolin-3-one; 69-85 wt % magnesium sulfate, on an anhydrous basis; (c) 2.3-4.8 wt % of a metal nitrate, on an anhydrous basis; (d) 1.3-3 wt % magnesium chloride, on an anhydrous basis; and (e) 6.5-14 wt % water; and said method comprises combining 69-85 wt % magnesium sulfate, on an anhydrous basis, with 15-31 wt % of an aqueous biocide composition comprising: (i) 25-35 wt % of a mixture of 5-chloro-2-methyl-4-isothiazolin-3-one and 2-methyl-4-isothiazolin-3-one; (ii) 10-22 wt % of a metal nitrate; (iii) 8-14 wt % magnesium chloride; and (iv) 35-50 wt % water.

7. The method of claim 6 in which the metal nitrate is magnesium nitrate and in which 5-chloro-2-methyl-4-isothiazolin-3-one and 2-methyl-4-isothiazolin-3-one are in a weight ratio from 2:1 to 4:1.

8. A solid microbicidal composition comprising: (a) 2.5-5.5 wt % of a mixture of 5-chloro-2-methyl-4-isothiazolin-3-one and 2-methyl-4-isothiazolin-3-one; (b) 60-85 wt % magnesium sulfate, on an anhydrous basis; (c) 3.7-8 wt % of a metal nitrate, on an anhydrous basis; (d) 1.2-2.5 wt % magnesium chloride, on an anhydrous basis; and (e) 10-22 wt % water.

9. A solid microbicidal composition comprising: (a) 2.5-26 wt % of a mixture of 5-chloro-2-methyl-4-isothiazolin-3-one and 2-methyl-4-isothiazolin-3-one; (b) 48-95 wt % magnesium sulfate, on an anhydrous basis; and (e) 2.5-26 wt % water.

* * * * *